(12) United States Patent
Wilson et al.

(10) Patent No.: US 7,045,679 B1
(45) Date of Patent: May 16, 2006

(54) TRANSGENIC PLANTS

(75) Inventors: Herbert Martin Wilson, Ames, IA (US); Bruce Marvin Held, Ames, IA (US); Harry Henry Stine, Adel, IA (US)

(73) Assignee: Stine Biotechnology, Inc., Ames, IA (US)

( * ) Notice: Subject to any disclaimer, the term of this patent is extended or adjusted under 35 U.S.C. 154(b) by 0 days.

(21) Appl. No.: 09/140,886

(22) Filed: Aug. 26, 1998

(51) Int. Cl.
*C12N 15/82* (2006.01)
*C12N 15/29* (2006.01)
*A01H 1/00* (2006.01)
*A01H 5/00* (2006.01)

(52) U.S. Cl. .................. 800/275; 800/278; 800/290; 800/320.1; 435/424; 435/468

(58) Field of Classification Search ........... 800/278, 800/279, 280, 281, 282, 283, 284, 285, 289, 800/290, 295, 298, 269, 320, 320.1, 275; 435/470, 468, 424
See application file for complete search history.

(56) References Cited

U.S. PATENT DOCUMENTS 5,288,626 A   2/1994   Levengood ............... 800/292

FOREIGN PATENT DOCUMENTS

EP           299552    *   1/1989
WO        WO 98/32326      7/1998

OTHER PUBLICATIONS

Masoud et al. Plant Molecular Biology. 1993. vol. 21: 655-663.*
Hamilton et al. Proc. Natl. Acad. Sci. 1996. vol. 93: pp. 9975-9979.*
Holl et al. Euphytica 32(1): 171-176, 1983.*
Kamra et al. Arch. Int. Physiol. Biochim. 85(5): 986-987, 1977.*
Korohoda et al. Z. Pflanzenphysiol. 94: 95-99, 1979.*
Turbin et al. Mutation Research 27: 59-68, 1975.*
Soyfer, V. Theor. Appl. Genet. 58(5): 225-235, 1980.*
Zhou, G. pp. 240-250 In: Exper. manip. ovule tissues, Chapman et al., eds., Longman: New York, 1986.*
Ishida, Y. et al., *Nature Biotechnology* 14:745-750 (1996) appears to relate to transformation of maize inbred A188 mediated by *Agrobacterium tumefaciens*.
Hamilton, C.M., *Gene* 200:107-116 (1997) appears to relate to construction of a binary-BAC vector suitable for *Agrobacterium* mediated plant transformation with high-molecular-weight DNA.
Hamilton, C.M. et al., *Proc. Natl. Acad. Sci. USA* 93:9975-9979 (1996) appears to relate to plant transformation with a binary-BAC vector.
Woo, S. et al., *Nucleic Acids Research* 22(2):4922-4931 (1994) appears to relate to the construction and characterization of a DNA library of *Sorghum bicolor*.
Woo, S. et al., *Plant Molecular Biology Reporter* 13(1):82-94 (1995) appears to relate to isolation of megabase-size DNA from *Sorghum* and its use in construction of BAC and YAC libraries.
Hu, Ching-yeh, and Lianzheng Wang (1999). "In Planta Soybean Transformation Technologies Developed in China: Procedure, Confirmation and Field Performance." *In Vitro Cell. Dev. Biol-Plant* 35:417-420.
Potrykus, Ingo (1989). "Gene transfer to cereals: an assessment." *Bio/Technology*. 8::535-538 (shown as pp. 269-273).
Mendel, R.R., and Teemu, H.T. (1995). "Barley, wheat, oat and other small-grain cereal crops." In. *Transformation of Plants and Soil Microorganisms*. Eds. Wang, K., et al. pp. 81-98.

* cited by examiner

Primary Examiner—David T. Fox
(74) Attorney, Agent, or Firm—Jondle & Associates, P.C.

(57) ABSTRACT

The present invention is related to transgenic plants having improved traits and to a method for producing such plants. The method involves the incorporation of large fragments of DNA from a donor species of plant into a recipient species of plant and selecting plants with improved traits.

16 Claims, No Drawings

TRANSGENIC PLANTS

BACKGROUND OF THE INVENTION

The present invention relates to transgenic plants having improved traits and to a method for producing such plants. The method involves the incorporation of large fragments of DNA from one species of plant into a second species of plant and selecting plants with improved traits.

The publications and other materials used herein to illuminate the background of the invention, and in particular, cases to provide additional details respecting the practice, are incorporated by reference, and for convenience are referenced in the following text by author and date and are listed alphabetically by author in the appended list of references.

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size is important.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pure line cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of corn breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. Unpredictability results from the fact that the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using identical original parents and the same selection techniques. This unpredictability results in the expenditure of large amounts of research money to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g. cultivar) and the desirable trait transferred from the donor parent.

Descriptions of other breeding methods that are commonly used for different traits and crops can be found in one of several reference books (e.g. Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parents is maintained. A single cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B) and (C×D). Much of the hybrid vigor exhibited by $F_1$ hybrids is lost in the next generation ($F_2$). Consequently, seed from hybrid varieties is not used for planting stock.

Recent advances in molecular biology have dramatically expanded the breeder's ability to manipulate the germplasm with which he is working. Genes controlling specific phenotypes, for example specific polypeptides that lend disease resistance or herbicide resistance, have been located within certain germplasm and isolated from it. Even more important has been the ability to take the genes which have been isolated from one organism and then introduce them into another organism. This transformation may be accomplished even where the recipient organism is from a different phylum, genus or species from that which donated the gene.

The development of these techniques has enabled the genetic engineering of desired traits by the introduction of exogenous genes into plant genomes. The uptake of new DNA by recipient cells has been accomplished by various means, including Agrobacterium infection (Nester et al., 1984), polyethylene glycol mediated DNA uptake (Lorz et al., 1985), electroporation of protoplasts (Fromm et al., 1986) and microprojectile bombardment (Klein et al., 1987). The transformed cells are selected, cultured and regenerated to form fertile transgenic plants. The transgenic plants are then introduced into the breeder's program to develop agronomically useful varieties which contain the new gene, using such breeding techniques as previously described. Transgenic plants of most, it not all, cultivated plant species have been produced using such genetic engineering techniques.

Tissue culture of corn is described in U.S. Pat. Nos. 4,665,030, 4,806,483 and 4,843,005. Corn tissue culture procedures are also described in Green and Rhodes (1982). Transformation of corn is described in U.S. Pat. Nos. 5,384,253, 5,489,520, 5,538,877 and 5,550,318. Corn transformation is also described by Prioli and Sondahl (1989) and Shillito et al. (1989).

Although transgenic plants are routinely prepared, the conventional process involves the isolation of a gene coding for a desired trait, the introduction of that gene into the particular germplasm of interest, regeneration of fertile plants and incorporation of the transgenic plants into the breeding program for analysis and development of agronomically acceptable varieties or hybrids. The identification and isolation of a gene coding for a desired trait can be very time consuming. In addition, the breeder must assess the effects of the inserted gene on the agronomic traits of the original germplasm, and must minimize such effects through breeding if plants with the new gene are to be agronomically acceptable to the grower.

It is desired to develop transgenic plants which does not require the isolation of specific genes for a desired trait. In accordance with the present invention, transgenic plants containing exogenous DNA having useful traits are prepared without the isolation of specific genes.

SUMMARY OF THE INVENTION

The present invention relates to transgenic plants having improved traits and to a method for producing such plants. The method involves the incorporation of large fragments of DNA from one species of plant into a second species of plant and selecting plants with improved traits. More specifically, DNA is isolated from one plant species, e.g. sorghum, and fragmented. The large fragments of DNA are then used to transform plant cells, e.g. corn, using conventional techniques, and transgenic plants are regenerated. The transgenic plants are grown in the field and analyzed for the expression of desired traits. Plants expressing desired traits are then introduced into a breeding program for the development of agronomically acceptable varieties and hybrids. Useful traits which can be introduced into recipient germplasm by this technique, include but are not limited to, increased resistance to drought conditions and heat stress, increased resistance to infestation by insect pests, increased standability, increased vigor, superior resistance to bacterial and fungal pests, superior combinability and superior yield.

DETAILED DESCRIPTION OF THE INVENTION

The present invention relates to transgenic plants having improved traits and to a method for producing such plants. In general, the method involves the incorporation of large fragments of DNA from one species of plant, the donor species, into a second species of plant, the recipient species, and selecting transgenic plants with improved traits. More specifically, in accordance with the method of the present invention, DNA is isolated from the donor plant species, e.g. sorghum, and fragmented. The large fragments of DNA are then used to transform plant cells of the recipient plant species, e.g. corn, using conventional techniques, and transgenic plants are regenerated. The transgenic plants are grown in the field and analyzed for the expression of desired traits. Plants expressing desired traits are then introduced into the breeding program for the development of agronomically acceptable varieties and hybrids.

Useful traits to be identified in the field include: increased resistance to drought conditions and heat stress, increased resistance to infestation by insect pests including European corn borer and corn root worm, increased standability, increased vigor, and superior resistance to bacterial and fungal pests. Individual plants can also show superior combining ability and produce higher yields in combination with other inbred lines. All of the improvements will be attributable directly or indirectly to the presence of certain large fragments of DNA from the donor species integrated into the recipient species' genome, this attribution indicated by the segregation of the useful trait with the introduced donor fragment.

Introduction of uncharacterized large fragments of DNA isolated from one species and transformed into another can be used to improve any crop plant where the technology exists to produce such transformants. Examples include, but are not limited to, introgression of genes from: *Hordeum bulbosum* into *Hordeum vulgare* for the improvement of barley; *Avena barbata* into *Avena sativa* for the improvement of oats; *Aegilops ventricosa*, *A. umbellata*, *A. comosa*, *A. variabilis* or *A. sharonensis*, into *Triticum aestivum* for the improvement of wheat; *Nicotiana repanda* into *Nicotiana tabacum* for the improvement of tobacco; *Gossypium stocksii* into *G. hirsutum* for the improvement of cotton; *Lycopersicon hirsutum* into *Lycopersicon aesculentum* for improvement of tomato; *Zea diploperennis*, *Z. mexicana*, *Tripsacum* spp, *Sorghum bicolor* into *Zea mays* for the improvement of corn; *Sorghum arundinaceum*, *Zea Mays*, *Trpisacum* spp into *Sorghum bicolor* for the improvement of sorghum. Examples are not limited to related species, nor to transfers between wild and cultivated species. Genes may be moved and tested in this manner from any plant species (donor) to any other plant species (recipient).

Large fragments (20 kb to 500 kb) may be introduced singly, or as part of the introduction of the entire genome. In accordance with the present invention, the production of transgenic plants is enhanced since no characterization at the DNA level is required. Transgenic plants having useful agronomic traits are selected in the field, i.e., the useful transgenic plants are determined by the phenotype of the transgenic plants in the field.

The present invention will be described with reference to sorghum as the donor species and corn as the recipient species. However, it is understood that this description is merely illustrative and the invention is applicable to any donor species and any recipient species. In accordance with the present invention, transgenic corn containing fragments of sorghum DNA is produced. An average of 50% of the cultured embryos produced clones from which fertile transgenic plants are obtained. With this frequency of response, all 5000 fragments (with an average size of 150 kb) in a sorghum BIBAC library are introduced into the corn genome and each fragment is then evaluated for its effect on the phenotype of elite corn inbreds and hybrids. Co-ordinate gene expression on the fragments in the transgenic plants allows sorghum traits to be evaluated in corn. As previously described, precise knowledge of gene action and expression, and of the location of genes in the corn and sorghum genomes, is not required for the present invention to produce transgenic plants having improved agronomic characteristics. The requirement to evaluate specific sorghum sequences is met by the introduction of the entire sorghum genome in large fragments (averaging 150 kb in size) into the corn genome ensuring that all sorghum genes are tested. Several methods may be employed to analyze at the molecular level the integration of sorghum DNA into the corn genome. Methods include but are not limited to Southern blots, polymerase chain reaction (PCR) based assays, and/or DNA sequencing. Of these, Southern blot analysis is the most common method used to evaluate the presence of foreign DNA in a genome. PCR based methods require sequence information that may not be available, and sequencing of 150 kb is time consuming and expensive. A complication in the molecular analysis is that the sorghum DNA shares a high degree of homology with corn DNA. Consequently, it is likely that short probes (i.e., 50 to 200 nucleotides) or primers that hybridize only to sorghum DNA will be used in analyses. Briefly, Southern blots involve the isolation of total DNA from the transgenic plant, cutting the DNA with a restriction enzyme, separating the DNA on a agarose gel using electrophoresis, and transferring the DNA from the agarose gel onto a membrane that can then be probed with Sorghum DNA used to transform the plant. Regions such as 3' untranslated regions of genes tend to be unique and would work particularly well as probes for this type of analysis.

Transgenic regenerants are selfed or backcrossed and the progeny planted in rows in the field. Selectable markers such as the bar gene from *Streptomyces hygroscopicus* for resistance to the Liberty™ herbicide, the mutant maize ahas gene (serine to asparagine at amino acid position 621) for resistance to Pursuit™ herbicide, the CP4EPSPS gene from *Agrobacterium* sp. CP4 for resistance to Round-Up™ herbicide can be introduced with the sorghum fragments to facilitate selection in the field. Spraying with the appropriate herbicide can be used to identify the transgenic segregants. If selectable markers are not introduced with the sorghum DNA, transgenic plants are grown in the field or greenhouse and analyzed for segregants in any measurable trait, including, but not limited to, maturity, drought resistance, cold hardiness, increased pest resistance, increased disease resistance, stalk strength, root strength, stay green, and the like. Transgenic segregants which show improved agronomic qualities can be selected for further evaluation both as inbreds and in hybrid combination. Generally, segregants with desirable changes are selected and selfed. Plants homozygous for the transgenes are then crossed with tester inbreds and hybrid yield evaluated. All transgenic segregants will potentially have an altered yield. In this manner, new inbreds and hybrids are produced having desirable agronomic characteristics.

EXAMPLES

The present invention is described by reference to the following Examples, which are offered by way of illustration and is not intended to limit the invention in any manner. Standard techniques well known in the art or the techniques specifically described below were utilized.

Example 1

Construction of a Library in *Agrobacterium* Containing 20 kb Fragments of Sorghum DNA Large molecular weight genomic DNA (100 kb) is isolated from Sorghum. Briefly, two grams fresh weight of tissue is frozen in liquid nitrogen and pulverized. Ground tissue is suspended in lysis buffer containing 20 mM EDTA, 10 mM Tris, pH 7.9, 1% Triton, 500 mM guanidine-HCL and 200 mM NaCl. This mixture is gently agitated at 37°–46° C. for 1–2 h. DNase-free RNase A is added to the concentration of 20 µg/ml and allowed to digest for 30 min at 370° C. Then proteinase K is added to the concentration of 0.8 mg/ml and all allowed to digest for 2 h. at 50° C. After centrifugation for 20 min. at 12–15,000×g, total genomic DNA is isolated using Qiagen columns according to the manufactures recommendation. Fragmentation of the DNA is accomplished by partially digesting the DNA with the restriction enzyme HindIII as is common to the art. Partially digested DNA is fractionated on a 0.7% agarose gel and DNA fragments around 20 kb are isolated from the gel using the Qiaex II gel extraction procedure following the instructions by the manufacturer Qiagen. Partially digested plant DNA is then ligated to plasmid pSB 12HBARGUS, which has been digested with HindIII and dephosphorylated to prevent self ligation. As a result the sorghum DNA is ligated between the bar and gus expression cassettes, thus, expression of Bar and Gus protein is a good indicator of the inclusion of sorghum DNA into the corn genome. The resulting ligated products are transformed into transformation competent HB101 *E. coli* according to the manufacturer Gibco BRL's instructions. Individual colonies are analyzed for an insert by isolating plasmid DNA by standard mini-prep procedures, digesting it with HindIII restriction enzyme, and analyzing it on a 0.7% agarose gel. The plasmids are then mobilized into *Agrobacterium* strain LBA 4404 containing plasmid SB1, which harbors the vir genes C, G, and B, via triparental mating as described by Ditta et. al. (1980). During triparental mating pSB 12HBARGUS containing sorghum DNA combines with SB 1 via homologous recombination and is stably maintained thereafter in *Agrobacterium* and is ready to be used to transform corn.

Example 2

Construction of a BIBAC Library in *Agrobacterium* Containing Greater than 100 kb Fragments of *Sorghum* DNA The first step in constructing a library harboring sorghum-DNA-fragments larger than 100 kb 15, requires the isolation of megabase size DNA as described by Woo et. al., 1995. Briefly, sorghum protoplasts are isolated from young leaf tissue, embedded in an agarose matrix using microbeads or agarose plugs, followed by cell lysis and protein degradation. DNA is made ready for cloning according to methods used to construct a bacterial artificial chromosome (BAC) library as described by Woo et. al., 1994. Briefly, the sorghum DNA is fragmented by partially digesting it with the restriction enzyme HindIII and separated on a low melting point agarose gel by pulse-field gel electrophoresis (PFGE). DNA ranging from 300–500 kb is isolated from the gel and used to ligate to the plasmid that has the essential features of a BIBAC vector as described by Hamilton, 1997, which includes a unique restriction site between the bar and gus expression cassettes (see Example 1). Plasmid is prepared for cloning by digesting with the same enzyme used to partially digest the megabase sorghum DNA and dephosphorylated as typically done to prevent self ligation. The ligation is performed according to Woo et al., 1994 and the resulting ligated products electroporated into electroporation competent *Agrobacterium* containing the plasmid pSB 1, which harbors the vir genes C, G, and B. Randomly picked clones are analyzed for insert size by isolating the DNA by standard mini-prep procedures, digesting it with a restriction enzyme that liberates the sorghum DNA fragment, and subjecting it to PFGE before it is used for the transformation of corn. Given an average insert size of 150 kb it would take 5000 clones to generate a genomic equivalent of the *Sorghum* genome given is $7.5 \times 10^8$ base pairs.

Example 3

Introduction of Sorghum BIBAC into Corn Through *Agrobacterium*-Mediated Transformation Sorghum BIBAC was introduced into corn through *Agrobacterium*-mediated transformation as modified from the procedure of Ishida et al. (1996). Briefly, immature embryos of the Stine inbred line 963 were aseptically removed from kernels of plants grown in a grow room (15 h photoperiod, 28° day and 25° night). Embryos were harvested 10 to 11 days after pollination when they were between 1 mm and 2 mm in length and then placed in 2 ml of LS-inf (Table 1) medium in an Eppendorf tube. The mixture was then stirred with a vortex mixer (Vortex Genie 2) at full speed for 5 seconds, the LS-inf medium removed and replaced with fresh medium, and then stirred again. All medium was then removed from the tube using a Pasteur pipette. Bacteria were collected with a platinum loop (enough to coat the wire of the loop) and thoroughly suspended in 1 ml of LS-infAS medium (Table 1) using a Pasteur pipette. The bacterial suspension was then introduced into the tube containing the embryos and the mixture stirred with a vortex mixer at full speed for 30 seconds. After this the embryos were allowed to stand for five minutes and were then transferred to the surface of LSAS medium solidified with agar (Table 1), care being taken to remove any accompanying liquid. Embryos were immediately oriented so that the scutellar surface was uppermost.

TABLE 1

| | LS Media Compositions | | |
|---|---|---|---|
| Ingredients/L | LSAS | LS-inf | LS-infAS |
| MS salts/vits[1] | 4.43 g | 4.43 g | 4.43 g |
| Proline | 700 mg | | |
| Casamino Acids | | 1.00 g | 1.00 g |
| Na$_2$EDTA | 37.3 mg | 37.3 mg | 37.3 mg |
| 2,4-D | 1.5 mg | 1.5 mg | 1.5 mg |

TABLE 1-continued

| | LS Media Compositions | | |
|---|---|---|---|
| Ingredients/L | LSAS | LS-inf | LS-infAS |
| MES | 500 mg | | |
| Thiamine HCl | | 1.0 mg | 1.0 mg |
| Sucrose | 20 g | 68.5 g | 68.5 g |
| Glucose | 10 g | 36.0 g | 36.0 g |
| Acetosyringone | 100 µM | | 100 µM |
| Phytagar | 7 g | | |
| pH | 5.8 | 5.2 | 5.2 |

[1]MS salts - Sigma Plant Culture Catalogue ref. M5519

The embryos were then cultured in the dark at 19° C. for 48 hours. After this time the plates were removed from the incubator and placed at 45° for 30 minutes. Then they were returned to the 19° C. incubator for a further day. Following this the embryos were transferred to DN62ALC medium (Table 2) and incubated at 24° C. for 5 days. Next, the embryos were transferred to DN62ALCB medium (Table 2) and incubated at 24° C. for 14 days. For the next 14-day passage the cefotaxime concentration was raised from 50 mg/l (in DN62ALCB medium) to 250 mg/l. This medium—DN62ACB—allowed for a better control of the residual *Agrobacterium* cells contaminating the corn embryos. Embryos were then transferred back to DN62ALCB medium for a further 14 days. At this time, transformed corn clones could be recognized by their ability to grow as prolific Type II callus on the bialaphos-containing medium. Culture of the clones continued on DN62B medium (Table 2) for a further two weeks after which time the Type II callus was transferred to DNROB medium (Table 3) to initiate regeneration. After one to two weeks on DNROB medium, somatic embryos developed as individual structures. These embryos were allowed to mature for one to two weeks on a further passage on DNROB medium (Table 3) and were then transferred to 0.5M ABA6S medium (Table 3). Finally, they were transferred to MSOG medium or 1/2MS 0.1IBA medium (Table 3) where they germinated and formed plantlets. The plantlets were then transferred to tubes containing 1/2MS 0.1IBA medium where roots developed. The plants were transferred to peat pots prior to going into the greenhouse. In the greenhouse, the plants were grown to maturity and seed collected either after backcrossing to Stine inbred 963 or after selfing.

TABLE 2

| | DN62 Media Compositions | | | |
|---|---|---|---|---|
| Ingredients/L | DN62B | DN62ALC | DN62ALCB | DN62ACB |
| N6 salts[1] | 3.98 g | 3.98 g | 3.98 g | 3.98 g |
| N6 vitamins[2] | 1 ml | 1 ml | 1 ml | 1 ml |
| Asparagine | 800 mg | 800 mg | 800 mg | 800 mg |
| Myo-inositol | 100 mg | 100 mg | 100 mg | 100 mg |
| Proline | 1400 mg | 1400 mg | 1400 mg | 1400 mg |
| Casamino Acids | 100 mg | 100 mg | 100 mg | 100 mg |
| 2,4-D | 1 mg | 1 mg | 1 mg | 1 mg |
| Sucrose | 20 g | 20 g | 20 g | 20 g |
| Glucose | | 10 g | | |
| AgNO₃ | | 10 mg | 10 mg | 10 mg |
| Bialaphos | 1 mg | | 1 mg | 1 mg |
| Cefotaxime | | 50 mg | 50 mg | 250 mg |
| Gelrite | 3 g | 3 g | 3 g | 3 g |
| pH | 5.8 | 5.8 | 5.8 | 5.8 |

[1]N6 salts - Sigma Plant Culture Catalogue ref. C 1416
[2]N6 vitamins: 2 mg/l glycine, 0.5 mg/l nicotinic acid, 0.5 mg/l pyridoxine HCl, 1 mg/l thiamine HCl (Chu, 1978).

TABLE 3

| | Regeneration Media Compositions | | | |
|---|---|---|---|---|
| Ingredients/L | DNROB | 0.5MABA6S | MSOG | 1/2MS 0.1IBA |
| MS Salts[1] | 4.43 g | 4.43 g | 4.43 g | 2.215 g |
| Asparagine | 800 mg | | | |
| Proline | 1400 mg | | | |
| Na₂EDTA | 37.3 mg | 37.3 mg | 37.3 mg | 37.3 mg |
| Casamino Acids | 100 mg | | | |
| Nicotinic Acid | 0.5 mg | | | |
| Gibberellic Acid | | | 0.1 mg | |
| Chloramben | | 0.5 mg | | |
| Abscisic acid | | 0.1 mg | | |
| Indole-3-Butyric Acid | | | | 0.1 mg |
| Sucrose | | 60 g | 30 g | 20 g |
| Sorbitol | 20 g | | | |
| Bialaphos | 1 mg | | | |
| Gelrite | 2 g | | | |
| Phytagar | | 7 g | 7 g | 7 g |
| pH | 5.8 | 5.8 | 5.8 | 5.8 |

[1]MS Salts - Sigma Plant culture Catalogue ref. M5519

Using this scheme, an average of 50% of the cultured embryos produced clones from which fertile transgenic plants are obtained. With this frequency of response, all 5000 fragments (with an average size of 150 kb) in the sorghum BIBAC library are readily introduced into the corn genome and each fragment can then be evaluated for its effect on the phenotype of elite corn inbreds and hybrids. Co-ordinate gene expression on the fragments in the transgenic plants allows sorghum traits to be evaluated in the transgenic corn. The requirement to evaluate specific sorghum sequences is met by the introduction of the entire sorghum genome in large fragments (averaging 150 kb in size) into the corn genome ensuring that all sorghum genes are tested.

Example 4

Analysis for the Presence of Sorghum DNA Fragments in Corn

Analysis is carried out on a few transgenic plants to exemplify that indeed large intact fragments of sorghum DNA have been integrated into the corn genome via transformation with *Agrobacterium*. In the transformation vector pSB 12HBARGUS (see Examples 1 and 2) the marker genes bar and gus straddle the unique HindIII cloning site in which the sorghum DNA is cloned. Therefore, an indicator of the integration of the complete sorghum DNA fragment into the genome is the presence of both the bar and gus genes. Evaluation of the expression of these marker genes is easily done at the phenotypic level. Bar expression is demonstrated by the ability of the transgenic callus to grow on the selective agent bialaphos (see Example 3). In addition, a leaf paint assay is performed in which a 1% solution of the herbicide Liberty™ is painted on the leaf of a transgenic plant. The lack of herbicide damage indicates bar expression. Expression of gus is evaluated by a histochemical analysis. Callus or leaf tissue is incubated in the presence of the substrate X-gluc at the concentration of 0.5 mg/ml in 0.1 M sodium phosphate buffer pH 7.0 and 0.1% Triton-x-100 at 37° C. for overnight. The presence of dark blue color in the tissue indicates gus expression.

The integration of sorghum DNA into the corn genome is detected by Southern blotting using conventional procedures. Briefly, total DNA is isolated from the transgenic plant, the DNA is cut with a restriction enzyme, the DNA is separated on a agarose gel using electrophoresis, and the DNA is transferred from the agarose gel onto a membrane that can then be probed with sorghum DNA used to transform the plant. In view of the high degree of homology between sorghum DNA and corn DNA, a unique region of sorghum DNA, such as 3' untranslated regions of genes, are used as probes for confirming the integration of sorghum DNA into the corn genome. Southern blotting confirms that sorghum DNA is integrated into corn DNA by this method.

Example 5

Field Evaluation of Transgenic Corn Plants

Seed collected from transgenic regenerants which had been selfed or backcrossed to the parental line Stine inbred 963 is field planted and plants evaluated. In this example, transgenic events are evaluated using the segregation of the bar gene, one of the markers on the vector into which the sorghum DNA is inserted for transformation. If a marker gene is not utilized, transgenic events are evaluated using segregation of characteristics of interest. Those events which show Mendelian segregation for single copy insertion are chosen for further evaluation in the field. Segregants show variation for traits such as time to reach maturity, drought resistance, cold hardiness, increased pest resistance, and stalk and root strength. Segregants with desirable changes are selected and selfed in a conventional breeding program. Plants homozygous for the transgenes are then crossed with tester inbreds and hybrid yield evaluated. All transgenic segregants potentially have an altered yield. In this manner, novel inbreds and hybrids are developed having improved agronomic traits resulting from the incorporation of sorghum DNA into the corn genome.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Allard, R. W. (1960). *Principles of plant breeding*, Wiley, New York.

Chu, C. C. (1978). "The N6 medium and its application to anther culture of cereal crops." In *Proc. Symp. on Plant Tissue Culture*, Sci. Press, Beijing, pp 43–50.

Ditta, G. et al. (1980). *Proc. Natl. Acad. Sci. USA* 77:7347–7351.

Fehr, W. R. (1987). *Principles of Cultivar Development*, Macmillan, New York

Fromm, M. E. et al. (1986). *Nature* 312:791–793.

Green and Rhodes (1982). "Plant Regeneration in Tissue Culture of Maize." In *Maize for Biological Research*, W. F. Sheridan, ed., University of North Dakota, Grand Forks, N. Dak., pp 367–372.

Hamilton, C. M. et al. (1996). "Stable transfer of intact high molecular weight DNA into plant chromosomes." *Proc. Natl. Acad. Sci. USA* 93:997509979.

Ishida, Y. et al. (1996). "High efficiency transformation of maize (*Zea mays* L.) mediated by *Agrobacterium tumefaciens*." *Nature Biotechnology* 14:745–750.

Klein, T. M. et al. (1987). *Nature* 327:70–73.

Lorz, H. et al. (1985)). *Mol. Gen. Genet.* 199:178–182.

Nester, E. W. et al. (1984). *Ann. Rev. Plant. Physiol.* 35:387–413.

Prioli and Söndahl (1989). "Plant Regeneration and Recovery of Fertile Plants from Protoplasts of Maize (*Zea Mays* L.)." *Bio/technology* 7:589–594.

Shillito et al. (1989). "Regeneration of Fertile Plants from Protoplasts of Elite Inbred Maize." *Bio/technology* 7:581–587.

Simmonds, N. W. (1979). *Principles of crop improvement*, Longman, London, New York.

Sneep, J. and Hendrikson A. J. T. (1979). *Plant breeding perspectives*, Centre for Agricultural Publishing and Documentation, Wageningen.

Woo, S-S. et al. (1994). "Construction and characterization of a bacterial artificial chromosome library of *Sorghum bicolor*." *Nuc. Acids Res.* 22:4922–4931.

Woo, S-S. et al. (1995). "Isolation of Megabase-Size DNA from *Sorghum* and Applications for Physical mapping and Bacterial and Yeast Artificial Chromosome Library Construction." *Plant Mol. Biol. Reporter* 13:82–94.

U.S. Pat. No. 4,665,030.

U.S. Pat. No. 4,806,483.

U.S. Pat. No. 4,843,005.

U.S. Pat. No. 5,384,253.

U.S. Pat. No. 5,489,520.

U.S. Pat. No. 5,538,877.

U.S. Pat. No. 5,550,318.

What is claimed is:

1. A method for obtaining a transgenic maize plant which comprises:
   (a) preparing genomic DNA of greater than 20 kb from DNA of a donor sorghum plant species;
   (b) transforming plant cells of a recipient maize plant with said genomic DNA associated with at least one selectable marker;
   (c) selecting transformed maize plant cells;
   (d) regenerating maize plants from the transformed maize plant cells;
   (e) harvesting seed from the regenerated maize plants;
   (f) planting the harvested maize seed and growing the resultant maize plants;
   (g) analyzing the maize plants for improved agronomic characteristics; and
   (h) selecting maize plants having an improved agronomic characteristic.

2. The method of claim 1 which further comprises selfing said selected maize plants and harvesting resultant maize seed.

3. The method of claim 1, wherein seed is harvested from regenerated maize plants which have been backcrossed to the recipient maize plant.

4. The method of claim 1, which further comprises introducing said selected maize plants having an improved agronomic characteristic into a breeding program to produce progeny of said maize plants, said progeny maintaining said improved agronomic characteristic.

5. A transgenic maize plant produced by the process of claim 1, wherein said transgenic maize plant comprises said sorghum genomic DNA.

6. A transgenic maize plant produced by the process of claim 2, wherein said transgenic maize plant comprises said sorghum genomic DNA.

7. A transgenic maize plant produced by the process of claim 3, wherein said transgenic maize plant comprises said sorghum genomic DNA.

8. A transgenic maize plant produced by the process of claim 4, wherein said transgenic maize plant comprises said sorghum genomic DNA.

9. A method for obtaining a transgenic maize plant having an improved agronomic characteristic which comprises:
   (a) preparing genomic DNA of greater than 20 kb from DNA of a donor sorghum plant species;
   (b) inserting said genomic DNA into a vector;
   (c) transforming plant cells of a recipient maize plant with said vector containing said genomic DNA associated with at least one selectable marker;
   (d) selecting transformed maize plant cells;
   (e) regenerating maize plants from the transformed maize plant cells;
   (f) harvesting seed from the regenerated maize plants;
   (g) planting the harvested maize seed and growing the resultant plants;
   (h) analyzing the maize plants for improved agronomic characteristics;
   (i) selecting maize plants having an improved agronomic characteristic;
   (j) harvesting seed from said selected maize plants; and
   (k) introducing seed from said selected maize plants into a breeding program to produce progeny of said maize plants, said progeny maintaining said improved agronomic characteristic.

10. The method of claim 9, wherein said genomic DNA inserted into a vector is inserted between two selectable markers.

11. The method of claim 9, which further comprises selfing said selected maize plants after step (i) and harvesting resultant maize seed.

12. The method of claim 9, which further comprises backcrossing the recipient maize plant to said selected maize plants after step (i) and harvesting resultant maize seed.

13. A transgenic maize plant produced by the process of claim 9, wherein said transgenic maize plant comprises said sorghum genomic DNA.

14. A transgenic maize plant produced by the process of claim 10, wherein said transgenic maize plant comprises said sorghum genomic DNA.

15. A transgenic maize plant produced by the process of claim 11, wherein said transgenic maize plant comprises said sorghum genomic DNA.

16. A transgenic maize plant produced by the process of claim 12, wherein said transgenic maize plant comprises said sorghum genomic DNA.

* * * * *